United States Patent [19]

Higa et al.

[11] Patent Number: 4,859,782

[45] Date of Patent: Aug. 22, 1989

[54] MISAKINOLIDE COMPOSITIONS AND THEIR DERIVATIVES

[75] Inventors: Tatsuo Higa, Naha, Japan; Ryuichi Sakai, Vero Beach; May S. Lui, Sebastian, both of Fla.

[73] Assignee: Harbor Branch Oceanographic Institution, Inc., Ft. Pierce, Fla.

[21] Appl. No.: 51,127

[22] Filed: May 18, 1987

Related U.S. Application Data

[63] Continuation-in-part of Ser. No. 879,134, Jun. 26, 1986, abandoned.

[51] Int. Cl.[4] ............................................. C07D 323/00
[52] U.S. Cl. ..................................................... 549/267
[58] Field of Search ........................................ 549/267

[56] References Cited

FOREIGN PATENT DOCUMENTS 0000195  1/1988  World Int. Prop. O. .......... 549/267

*Primary Examiner*—Glennon H. Hollrah
*Assistant Examiner*—Amelia A. Owens
*Attorney, Agent, or Firm*—Carroll F. Palmer

[57] ABSTRACT

This invention relates to novel macrolide compositions which are useful as antitumor, antiviral and antifungal compositions, a process of producing the compositions and a method for inhibiting tumors, viruses and fungi utilizing the compositions. More particularly, the novel macrolide compositions are organic misakinolide and misakinolide derivative compositions which are derived from marine sponges genus Theonella.

10 Claims, No Drawings

MISAKINOLIDE COMPOSITIONS AND THEIR DERIVATIVES

FIELD OF THE INVENTION

This application is a continuation-in-part of Ser. No. 879,134 filed June 26, 1986, abandoned. This invention relates to new organic compositions which have useful antitumor, antiviral and antifungal activity Additionally and particularly, this invention relates to new antitumor, antiviral and antifungal misakinolide and derivative compositions derived from marine organisms, i.e., sponges of the genus Theonella and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

While certain methods and chemical compositions have been developed which aid in inhibiting, remitting or controlling the growth of tumors further antitumor methods and chemical compositions are needed.

Viral diseases inflict man, plants, insects, and animals. The prevention and control of viral diseases have important health and economic implications.

Viral diseases contribute to inflictions in humans including common colds, herpes and cancer and the importance of their control is obvious. Also important is control of viral diseases in animals for economic reasons as well as the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

Prevention of the growth of fungus and the infections and maladies caused by it to mammals and plants is also of importance to man. The presence of fungus may cause various diseases and infections in man including mycotic disease, e.g., pulmonary candidiasis and pulmonary blastomycosis. Certain yeastlike organisms, e.g., *Cryptococcus neoformans*, may cause serious infections of the central nervous system. More commonly known fungal infections in humans and mammals include ringworm, which are fungus infections of hair and nail areas, as well as resistant infections of the skin. Many other fungal infections inflict humans and mammals in the areas of skin, mucous membranes, intestinal tract, vaginal area and lungs.

Plants are also attacked by various fungi. Damage caused by fungus infection to agriculture amounts to billions of dollars annually. Various inorganic and organic fungistats and fungicides have been tried but with limited success. It is of course important for the fungistat or fungicide to kill the fungi but not the plant and to leave no toxic residue on the food of the plant. Various methods have been utilized to combat fungus infection in agriculture including foliage fungicide by which method plants are coated with a preventive weather-resistant fungicide. Seed treatment and soil treatment are methods which require fungicides which are safe for seeds and resist degradation by soil and soil microorganisms. Chemotherapeutants are fungicides which permeate the plant to protect new growth or eliminate infections which have already occurred within the plant. Agricultural fungistats and fungicides and their application must also meet very stringent requirements and regulations, which have been promulgated, for example, in the United States.

Considerable research and resources have been devoted to oncology and antitumor measures including chemotherapy; antiviral measures; and combating fungal infections in both mammals and plants. While various antitumor, antiviral or antifungal agents and methods have been developed which aid in inhibiting tumors, viruses and the spread of fungus, respectively, additional methods and chemical agents are needed.

A potential source for antiviral compositions is marine plant and animal life and of particular interest are marine sponges. It has now been found that certain organic compounds derived from extracts of sponges of the genus Theonella, possess useful antitumor, antiviral and antifungal activity.

Some compounds of interest have been previously isolated from marine sponges and alga. These compounds named swinholide-A and scytophycin A and B have been reported by S. Carmely and Y. Kashman, "Structure of Swinholide-A, a new macrolide from the Marine Sponge Theonella Swinhoei," *Tetrahedron Letters*, 26, 511–514 (1985) and R. E. Moore, G. M. L. Patterson, J. S. Mynderse, and J. Barchi, Jr. "Toxins from cyanophytes belonging to the Scytohemataceae" *Pure and Applied Chemistry*, 58, No. 2,263–271 (1986), respectively. The entire disclosures of these references is hereby incorporated herein by reference. Thus, marine sponges and other marine life can be a source of useful raw materials for man.

SUMMARY OF THE INVENTION

It is therefore an object of the invention to provide novel compositions which are useful as antitumor, antiviral and antifungal agents and a process for producing such novel compositions.

It is an additional object of the invention to provide a method for inhibiting tumors, viruses and fungus growth and resultant infection and disease utilizing novel antitumor, antiviral and antifungal compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula (I):

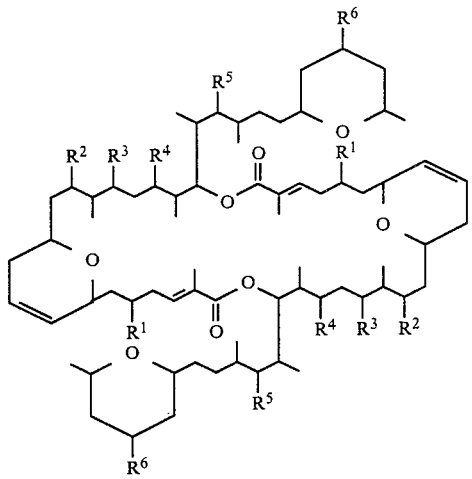

wherein $R^1$, $R^2$, $R^3$ $R^4$ $R^5$ and $R^6$ are the same or different and are a hydrogen, hydroxy, lower alkoxy, or lower acyloxy group. The invention also comprises reduced derivatives of these compositions wherein at least one of the double bonds of the composition described above according to formula I is reduced.

The invention also comprises compositions formed by the treatment of any of the compositions of formula I and their reduced derivatives with oxidizing reagents, such as Jones reagent or pyridinium chlorochromate (PCC); with alkaline solutions; and with acidic solution.

All of the above-described compositions according to formula I, as well as, their reduced derivatives and derivatives formed by treatment with Jones reagent, alkaline or acid solutions will collectively be referred to, hereinafter, as "macrolide compositions of the invention."

In preferred embodiments of the invention, the composition is substantially pure.

In preferred embodiment of the invention the lower alkoxy and acyloxy groups have from 1 to 5 carbon atoms. In further preferred embodiments of the invention, the invention comprises dimeric compositions of formulae II and III:

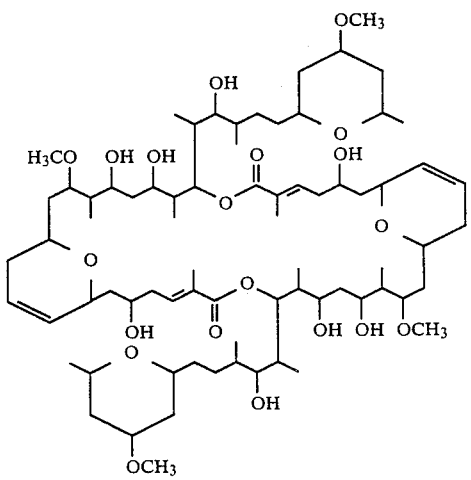

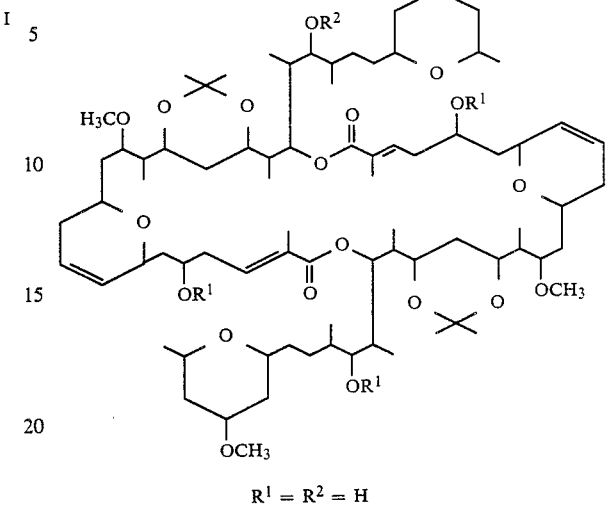

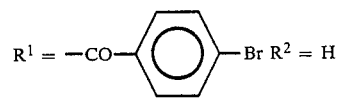

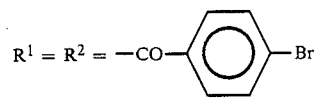

As embodied and fully described herein, the invention also comprises an antitumor, antiviral or antifungal composition comprising, as active ingredient, an effective antitumor, antiviral or antifungal amount, respectively, of one or more macrolide compositions of the invention and a non-toxic pharmaceutically acceptable carrier or diluent.

As embodied and fully described herein, the invention also comprises a process to produce the macrolide compositions of the invention. The process comprises the steps of collecting marine sponge of the genus Theonella, contacting the marine sponge with a suitable organic solvent system to obtain an extract; fractionating the extract; and isolating a macrolide composition of the invention from the fractionated extract.

As embodied and fully described herein, the invention further comprises a method for inhibiting tumors comprising contacting tumor cells with an effective antitumor amount of one or more macrolide compositions of the invention.

As embodied and fully described herein, the invention further comprises method for inhibiting viruses comprising contacting viruses with an effective antiviral amount of one or more macrolide compositions of the invention.

As embodied and fully described herein, the invention further comprises a method for inhibiting the growth of or killing fungi comprising contacting fungi with an effective antifungal amount of one or more macrolide compositions of the invention.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises macrolide compositions of the general formula I:

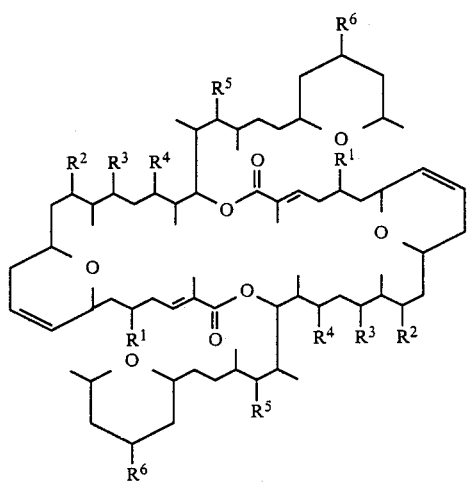

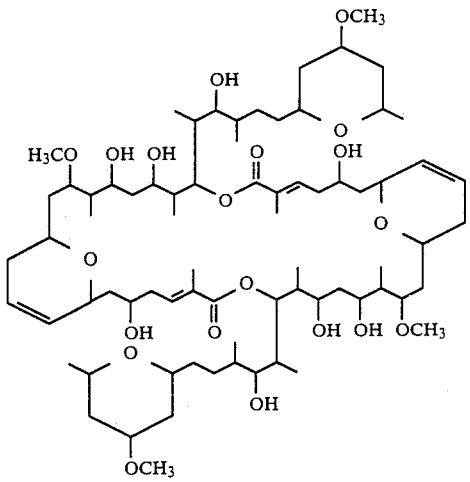

wherein $R^1$, $R^2$, $R^3$ $R^4$ $R^5$ and $R^6$ are the same or different and are a hydrogen, hydroxy, lower alkoxy, or lower acyloxy group. The invention also comprises reduced derivatives of these compositions wherein at least one of the double bonds of the composition described above according to formula I is reduced.

The invention also comprises compositions formed by the treatment of any of the compositions of formula I and their reduced derivatives with oxidizing agents, such as Jones reagent or PCC; with alkaline solutions; and with acid solutions. All of the above-described compositions are referred to herein as "macrolide compositions of the invention."

In preferred embodiments of the invention, the composition is substantially pure.

In preferred embodiments of the invention the lower alkoxy or acyloxy groups have from 1 to 5 carbon atoms. In more preferred embodiments of the invention, the invention comprises compositions of the formulae II and III:

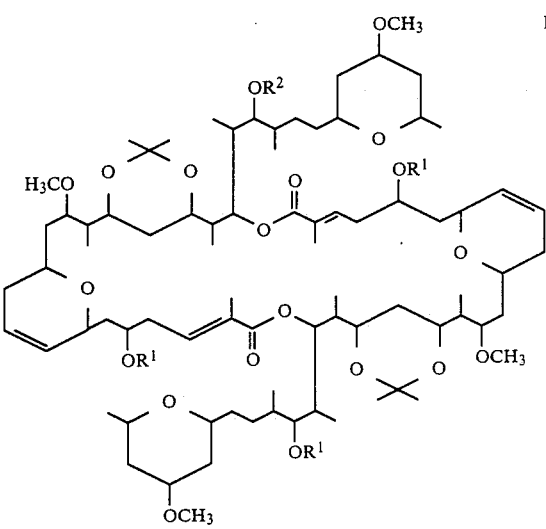

$R^1 = R^2 = H$

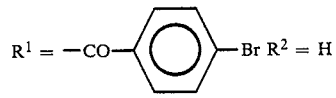

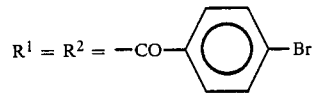

In accordance with the invention, an antitumor composition is provided comprising as active ingredient an effective antitumor amount of one or more of the macrolide compositions of the invention and a non-toxic pharmaceutically acceptable carrier or diluent. While effective amounts may vary, as conditions in which the antitumor compositions are used vary, a minimal dosage required for activity is generally between 0.01 and 10 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more macrolide compositions of the invention. The macrolide compositions of the invention are active for inhibiting a diverse range of tumors including, but not limited to human lung, colon and mammary tumors such as lung carcinoma A549, ileocecal adenocarcinoma HCT-8, and human breast adenocarcinoma cells MDA-MB-231. The effectiveness of the compositions of the invention for inhibiting tumors indicates their usefulness for controlling tumors in hosts including mammals and for treating cancerous cachexia.

In accordance with the invention, an antiviral composition is provided comprising as active ingredient an effective antiviral amount of one or more macrolide compositions of the invention and a non-toxic pharmaceutically acceptable carrier or diluent. While effective amounts may vary, as conditions in which the antiviral compositions are used vary, a minimal dosage required for activity is generally between 50 to 100 micrograms against 25 to 80 plague forming units of virus cells. The macrolide compositions of the invention are active for inhibiting or killing a diverse range of viruses including, but not limited to, RNA viruses, vesicular stomatitis (herein "VSV") adeno-, corona-, reo- and influenza viruses and the DNA virus, Herpes Simplex - I and II (herein "HSV-I" and "HSV-II") adeno- and papovaviruses. Useful examples of non-toxic pharmaceutically acceptable carriers or diluents include, but are not limited to, the following: ethanol, dimethyl sulfoxide and glycerol.

In accordance with the invention, a method for inhibiting viruses in a host is provided comprising contacting viruses with an antiviral amount of one or more macrolide compositions of the invention. The effectiveness of the macrolide compositions of the invention for inhibiting viruses indicates their usefulness for controlling viruses and virus related diseases in hosts including mammals.

In accordance with the invention, an antifungal composition is provided comprising as active ingredient an effective antifungal amount of one or more of the macrolide compositions of the invention and a non-toxic pharmaceutically acceptable carrier or diluent. While effective amounts may vary, as conditions in which the antifungal compositions are used vary, a minimal dosage required for activity is generally between 1 and 10 micrograms/ml against $10^3$/ml fungi, such as *Candida albicans* for example. Useful examples of non-toxic pharmaceutically acceptable carriers or diluents include, but are not limited to, the following: ethanol, dimethyl sulfoxide and glycerol.

In accordance with the invention, a method for inhibiting fungus in a host is provided comprising contacting fungus with an antifungal amount of one or more macrolide compositions of the invention. The effectiveness of the compositions of the invention for inhibiting fungus indicates their usefulness for controlling fungus and fungus related diseases in hosts including mammals. Further, such macrolide compositions may be useful as agricultural fungicides.

In accordance with the invention, a process is provided to produce the macrolide compositions of the invention. The process comprises the steps of collecting samples of the marine sponge of the genus Theonella, contacting the marine sponge with a suitable organic solvent system to obtain an extract; partitioning said extract by reverse phase chromotography to obtain a number of fractions; and isolating a macrolide composition of the invention from the fractionated extract.

In preferred embodiments of the invention the suitable organic solvent system is selected from the group of solvents consisting of acetone, ethyl acetate, methanol, toluene, methylene chloride, chloroform, methyl ethyl ketone, ethanol, methyl isobutyl ketone and mixtures thereof. Particularly preferred extracting solvents are acetone and ethyl acetate.

While those solvents listed above are the presently preferred choices for the solvents useful in accordance with the invention, other suitable solvents may be substituted. A suitable solvent system should be capable of extracting a macrolide composition of the invention from other components of the sponge. Different ratios of solvents and any combination may be used in the solvent system of the invention as would be known to those skilled in the art.

Compositions according to the invention are synthesized and/or isolated by various fractionation, synthetic and chromatographic techniques from the extracts obtained. Any suitable fractionation and isolation techniques as known to those skilled in the art may be utilized in accordance with the process of the invention. Suitable isolation techniques include various chromotography techniques such as high pressure liquid chromotography (HPLC) with suitable columns as would be known to those skilled in the art (e.g., an ODS column) eluted with a suitable solvent such as, for example, methanol.

A more detailed description and explanation of a preferred embodiment of the process of the invention to produce a macrolide composition of the invention is provided in the examples section.

It is therefore apparent that the macrolide compositions of the invention, the process for producing the macrolide compositions of the invention and the methods for utilizing the macrolide compositions of the invention to inhibit tumors, viruses and fungus growth fulfill the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention The following examples represent preferred embodiments of the compositions, processes and methods of the invention for satisfying the stated objects of the invention. The starting materials and reagents in the examples whose methods of preparation are not indicated are commercially available from sources known to the art such as chemical supply houses.

EXAMPLE 1

Preparation of Misakinolide (1) and derivatives thereof (2-4)

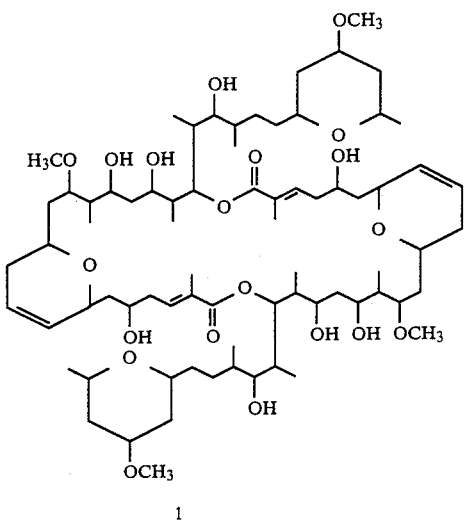

1

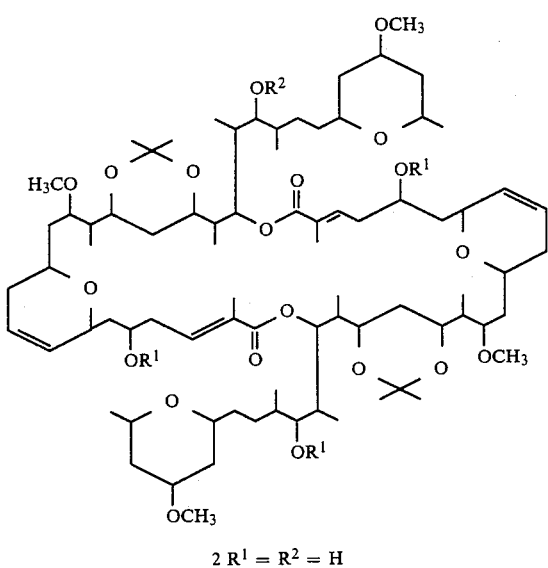

2  $R^1 = R^2 = H$

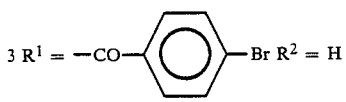

3  $R^1 = $ —CO—⟨⟩—Br  $R^2 = H$

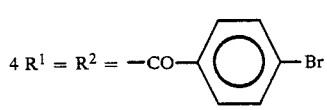

4  $R^1 = R^2 = $ —CO—⟨⟩—Br

A sample (320 g) of marine sponge of the genus Theonella, collected at Maedamisaki, Okinawa, was extracted by steeping in acetone (700 mL) for 48 hours. The extract was concentrated to give an aqueous suspension which on further extraction with ethyl acetate gave 0.5 g of ethyl acetate soluble oil. The oil showed strong in vitro antitumor activity against P388 mouse leukemia cells, HCT-8 human colon adenocarcinoma, A549 human lung carcinoma, MDA-MB-231 human breast cancer cells. The oil was separated using NS gel (polystyrene gel) and eluting with 20:1 methanol-water. Active fractions (185 mg) were combined and further separated over silica gel by eluting first with ethyl acetate and then with 5:1 methylene chloride-methanol. The latter eluate (64 mg) was purified by running on HPLC (ODS column, methanol) to give 24 mg of misakinolide as colorless oil, $[\alpha]_D^{20} -21.4°$ (c 5.6, $CHCl_3$). Misakinolide gave the following spectral data: UV (MeOH) $\lambda$max 220 nm ($\epsilon$ 5000); IR (film) 3440, 2960, 2935, 2820, 1680, 1635, 1455, 1380, 1260, 1195, 1150, 1125, 1080, 985, 970, 925, 850, 750, and 700 cm$^{-1}$; $^1$H NMR ($C_6D_6$) $\delta$ 7.30 (1H, m), 5.69 (1H, br d, J=7.9 Hz), 5.60 (1H, m), 5.55 (1H, br d, J=8 Hz), 4.71 (1H, br d, J=9 Hz), 4.23 (1H, m), 4.18 (1H, m), 4.03 (1H, m), 3.98 (1H, m), 3.88 (1H, m), 3.67 (1H, m), 3.53 (1H, m), 3.34 (3H, s), 3.33 (1H, m), 3.29 (1H, m), 3.15 (3H, s), 1.97 (3H, br s), 1.20 (3H, d, J=4.7 Hz), 1.10 (3H, d, J=5.0 Hz), 1.04 (3H, d, J=4.8 Hz), 1.02 (3H, d, J=5.1 Hz), and 0.95 (3H, d, J=5.0 Hz); $^{13}$C NMR ($C_6D_6$ 171.04 (s), 142.41 (d), 130.55 (d), 129.00 (s), 123.57 (d), 77.74 (d), 76.90 (d), 76.29 (d), 74.85 (d), 73.59 (d), 71.16 (d), 70.74 (d), 68.10 (d), 66.83 (d), 64.68 (d), 64 29 (d), 56.75 (q), 54.99 (q), 41.63 (t), 41.62 (d), 41.12 (d), 39.18 (t), 39.00 (t), 38.20 (t), 37.70 (d), 35.69 (t), 35.23 (t), 33.40 (d), 31.51 (t), 28.55 (t), 24.58 (t), 21.62 (q), 18.20 (q), 12.90 (q), 9.60 (q), 9.46 (q), and 9.46 (q).

EXAMPLES 2-4

Treatment of composition (1) with acetone and p-TsOH gives an acetonide (2). Treatment of acetonide (2) with p-bromobenzoyl chloride and pyridine gives a tribenzoate (3) and tetrabenzoate (4).

EXAMPLE 5

(1) Catalytic reduction

Misakinolide is reduced to a dihydro or tetrahydro derivative by catalytic reduction. A mixture of a sample of misakinolite and a small amount of catalyst such as Pd/C, Pt/C, or Raney Ni in methanol or ethanol is stirred under hydrogen atmosphere to give hydrogenation products.

(2) Reduction with lithium aluminum hydride (LiAlH$_4$)

Reduction of misakinolide with LiAlH$_4$ is carried out in dry ether or THF under usual (standard) conditions to yield a product containing a primary alcohol function formed by reduction of the lactonic carbonyl.

EXAMPLE 6

(1) Oxidation with Jones reagent

To a stirred solution of misakinolide in acetone or in ether is added Jones reagent prepared in acetone (see Bowers, Halsall, Jones, and Lemin, *J. Chem. Soc.*, 2548 (1953)) or in ether (see Brown, Garg, and Liu, *J. Org. Chem.*, 36, 387 (1971)) at room temperature. Depending on the amount of the reagent employed and duration of the reaction, products (ketones) are varied and are generally a mixture of several compounds unless the reaction is carried out with an excess of the reagent for a longer period.

EXAMPLE 7

A sample of misakinolide in ethanol is heated with potassium hydroxide. After cooling the mixture is acidified by adding hydrochloric acid solution and concentrated. The residue is partitioned between water and ether (or ethyl acetate). The organic phase is concentrated to give a carboxylic acid. If necessary, the product is purified by HPLC.

EXAMPLE 8

A sample of misakinolide in ethanol is heated with hydrochloric acid or sulfuric acid. After cooling and concentration the residue is partitioned between water and ether (or ethyl acetate). The organic layer is concentrated to give a mixture of several dehydration products and/or other acid-catalyzed reaction products which are separated by HPLC.

ANTITUMOR ACTIVITIES OF THE COMPOUNDS OF THE INVENTION

The following assay method was utilized to illustrate the antitumor effectiveness of the compositions of Formulae I and II corresponding to misakinolide of example 1.

P388 MOUSE LEUKEMIA CELL ASSAY

Maintenance of Cell Line

P388 mouse leukemia cells are grown in Dulbecco MEM medium with 10% horse serum, 4 mM glutamine, and 20 μg/ml gentamycin (Biologos, Inc.). Cells are incubated in 10% $CO_2$ and subcultured 2 times per week.

PROCEDURE

1. Add composition to each well of a 24-well plate or tube and allow solvent to evaporate to dryness.
2. Add 2 ml ($1.2 \times 10^5$) cells to each well or tube and mix.
3. Incubate in 10% $CO_2$ at 37° for 48 hours.
4. Read plates with an inverted microscope, scoring activity from 1+ to 4+ as follows: ND (not detectable), >90%; 1+, 75-90%; 25-49%; 4+, <25% of control growth. Alternatively, the activity may be designated as $IC_{50}$ concentration which is the concentration of composition required to inhibit 50% of cell growth on the plate. Cell counts are performed on each tube and results are reported as percent of control.

HUMAN TUMOR CELL LINE ASSAY

Maintenance of Cell Line

HCT-8 human colon tumor cells are growth in RPMl 1640 medium (GIBCO). A549 human lung carcinoma cells are cultured in Dulbecco medium (Biologos, Inc.). All media are supplemented with 10% fetal bovine serum and contain 50 μg/ml gentamycin. All human tumor cell lines are incubated at 5% $CO_2$ at 37° and subcultured once a week.

PROCEDURE

1. Seed lml cell (5000 HCT-8, 8000 A549, 12000 MCF-7) in each well of a 24-well plate.
2. Incubate in a $CO_2$-incubator for 48 hours.
3. Add composition to each well and incubate for an additional 120 hours.
4. Discard medium and stain with methylene blue (HCT-8) or crystal violet (A549 and MCF-7).
5. Compare cell density of drug-treated well with that of the control (no drug added) as follows: ND (not detectable), >90%; 1+, 75-90%; 2+, 50-74%; 3+, 25-49%, 4+, <25% of control growth.

Positive control—Vinblastine or Vincristine in aqueous solution.

Final Conc. of Vinblastine or Vincristine control (use 2 μl/assay)

| Solution Conc. | Amt added | Final conc. in test |
|---|---|---|
| 5 mg/ml | 2 μl | 5 μg/ml |
| 1 mg/ml | 2 μl | 1 μg/ml |
| 0.1 mg/ml | 2 μl | 0.1 μg/ml |
| 0.05 mg/ml | 2 μl | 0.05 μg/ml |

MDA-MB-231 human breast adenocarcinoma cell line is also utilized in substantial accordance with the above assay.

The results of the above assays are summarized in Table 1.

ANTIVIRAL ACTIVITIES OF THE COMPOSITIONS OF THE INVENTION

The following assay method was utilized to demonstrate the in vitro antiviral effectiveness of compositions of the invention as reported in Table 2.

Antiviral Disc Assay for HSV-1 and VSV

A. Maintenance of Cell Cultures
  1. Virus
    a. Both herpes simplex type 1 (HSV-1) and vesicular stomatitis virus (VSV) replicate in the CV-1 cell line. CV-1 is a fibroblast-like cell culture derived from primary African green monkey cells.
  2. Growth of CV-1 Cells
    a. Seed 150 $cm^2$ tissue culture flasks each with $10 \times 10^6$ CV-1 cells in 40 ml of EMEM with 10% FBS (growth medium).
    b. Seven days after seeding the flasks cell numbers should be approximately $40-50 \times 10^6$ cells CV-1 cells have a doubling time of 72 hours based on these numbers.
  3. Trypsinization
    a. Aseptically remove the medium.
    b. Rinse cell sheet with 10 ml of $Ca^{++}$ and $Mg^{++}$ free Dulbecco's phosphate buffered saline or Pucks G saline at least twice.
    c. Add 1.5 to 2.0 ml of trypsin -EDTA mixture.
    d. Incubate flask at room temperature or at 37° C. with occasional rocking until the cells detach from the flask (about 15-30 min). Cells maintained on calf serum detach from the plastic at a faster rate than those held on fetal bovine serum (FBS).
    e. Shake flask.
    f. Add 10 ml EMEM growth medium and break up cell clumps with pipetting.
    g. Count cells.
B. Preparation of plates for viral assays
  1. Cell Concentration
    a. Dilute the cells with EMEM to $4 \times 10^5$ cells/ml.
    b. Seed 24 well trays with 0.5 ml per well. Cell concentration per well is $2 \times 10^5$ cells.
    c. Incubate at 37° C with 5% $CO_2$.
    d. The wells can be uses over the next several days beginning the day after seeding (preferably 2, 3, or 4).
C. Assay of HSV-1 and VSV in CV-1 cells
  1. Infection of CV-1 cells in plates with virus
    a. Remove medium from wells.
    b. Infect well with at least 25 and no more than 80 plaque forming units (PFU) of virus.

c. Incubate infected cells at 37° C. for 1.5 hours.
d. Pour off supernatant at end of incubation period.
e. Add 0.5 ml of methylcellulose overlay medium (MCO).
   (1) MCO is a maintenance medium without phenol red made with 1% 4000 centipose methylcellulose. FBS is used at 5% level.
2. Drug Evaluation
   a. For drug evaluation wet filter paper discs (6 mm diameter) with approximately 0.02 ml of marine extract or test compound.
      (1) Allow solvent to evaporate for 20 to 30 minutes at room temperature.
      (2) Place discs in the well containing CV-1 cells, virus, and MCO.
   b. Incubate tissue culture plates for 48 hours at 37° C.
   c. After 48 hours place 0.5 ml NRMCO on each well.
      (1) NRMCO is a maintenance overlay medium without phenol red containing 0.1 mg neutral red dye per ml and 2% 15 centipoise methylcellulose.
   d. Incubate plates at 37 C and read the following day.
      (1) Antiviral activity should be observed from two parameters. One is actual reduction in the number of plaques and two is the diminution in plaque diameter.
3. Scoring Drug Activity
   a. Antiviral activity is scored from 0 to +++.
      +++ = complete inhibition of plaque formation
      ++ = partial inhibition
      + = partial inhibition
      0 = no protection
   b. Cytotoxicity
      0 = no visual or microscopic cytotoxicity
      16 = Complete cell destruction
      8, 10, 12, 14 = partial cytotoxicity

ANTIFUNGAL ACTIVITIES OF THE COMPOSITIONS OF THE INVENTION

The following assay method was utilized to demonstrate the in vitro antifungal effectiveness of compositions of the invention as reported in table 3.

Preparation of inocula

*Candida albicans:* *C. albicans*(Ca) is grown on Sabouraud dextrose agar to produce single colonies one of which is used to inoculate Sabouraud dextrose broth. The broth is incubated at 37° C. with shaking at 200 rpm for 18 hrs., the resultant culture is frozen with 10% (v/v) glycerol at −80° C. and used as the inoculum for the anti-Candida assay.

*Saccharomyces cerevisiae:* *S. cerevisiae* (Sc) is grown in a manner identical to that described for *C. albicans* except that all incubations are at 30° C.

*Penicillium atrovenetum:* Spores of *P. atrovenetum* (Pa) are inoculated onto the surface of V8 agar. Incubation at room temperature for approximately 1 week results in a mature fungal colony. The spores are harvested from this plate by washing with 0.1% (v/v) Triton X-100, spores are then washed with distilled water before freezing at −80° C. in the presence of 10% (v/v) glycerol.

Assay protocols

1. Disc diffusion assay

*C. albicans* or *S. cerevisiae* are inoculated into melted Sabouraud dextrose agar at 45° C. to give a cell density of approximately 1000 cells/mL. Plates are prepared with 10 mL of the seeded agar in a 10 cm × 10 cm petri dish. These plates are stored at 4° C. until needed for the assay.

*P. atrovenetum* spores are inoculated at 1000 conidia/mL into Tryptic Soy agar at 45° C. The remaining protocol is as described for the other microorganisms.

Paper discs (6.35 mm) are impregnated with the test substance and allowed to dry. They are then placed onto the surface of a test plate prepared as detailed above. Plates are incubated overnight (*C. albicans* 37° C.; *S. cerevisiae* 30° C.; *P. atrovenetum* 25° C.) after which time the zones of growth inhibition can be read, these are expressed as the diameter of the zone in millimeters.

2. Minimum inhibitory concentration (MIC)

Two-fold dilutions for the drug are prepared in 50 μL volumes of Sabouraud dextrose broth using 96-well microtiter plates An inoculum of *C. alibicans* is added in a small volume to give a cell density of approximately 1000 cells/mL. Plates are incubated at 37° C overnight. 10 μL of Triphenyl tetrazolium chloride (1% w/v) is then added to each well; a further 2 hour incubation results in a deep coloration of the microorganism. The MIC is the lowest concentration of the drug which has completely inhibited growth.

TABLE 1

| Antitumor activity P388 $IC_{50}$ 10 ng/ml | | | |
|---|---|---|---|
| Human cell activity | | | |
| Dose (ng/ml) | HCT-8 | A549 | MDA-MB-231 |
| 5 | 3+ | 3+ | 4+ |
| 1 | 1+ | 1+ | 4+ |

TABLE 2

| | Antiviral activity | | | |
|---|---|---|---|---|
| | VSV | | HSV-1 | |
| Dose (μg/well) | cyt | av | cyt | av |
| 8 | 0 | + | 0 | ++ |
| 4 | 0 | − | 0 | + |

TABLE 3

| Antifungal activity | | | |
|---|---|---|---|
| Dose (μg/disc) | Pa | Sc | Ca |
| 5 | 10 | 12 | 10 |
| Ca MIC: 5 μg/ml | | | |

The above data reports the in vitro activity of misakinolide for inhibiting tumors, viruses and fungi. The above results indicate that the macrolide compositions of the invention are useful for inhibiting tumors, viruses and fungi in hosts and the diseases caused thereby.

The scope of the present invention is not limited by the description, examples, and suggested uses herein and modifications can be made without departing from the spirit of the invention. The macrolide compositions of the present invention have a novel molecular skeleton from which many derivative compounds or series of compounds may be prepared The present invention contemplates such derivatives as modifications of the present invention and within the scope of the invention. For example, it may be noted that other derivatives of the compounds of example 1 such as halogen or alkyl substituted derivatives may be prepared that may possess antitumor, antiviral or antifungal activity analogous to those preferred embodiments described above. Further, the compositions described herein may have other useful applications such as, for example, analgesic applications or as starting materials for the preparations of other compositions. Therapeutic application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound of the formula:

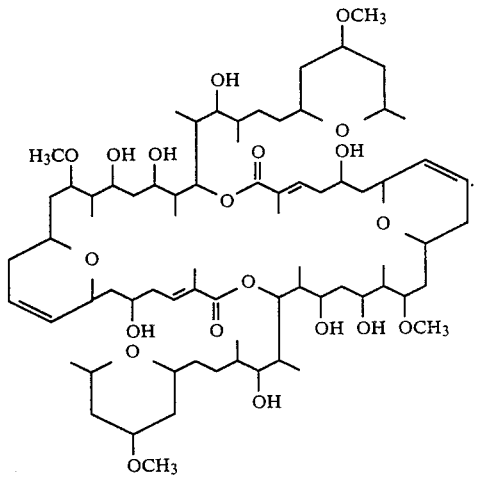

2. A compound of the formula:

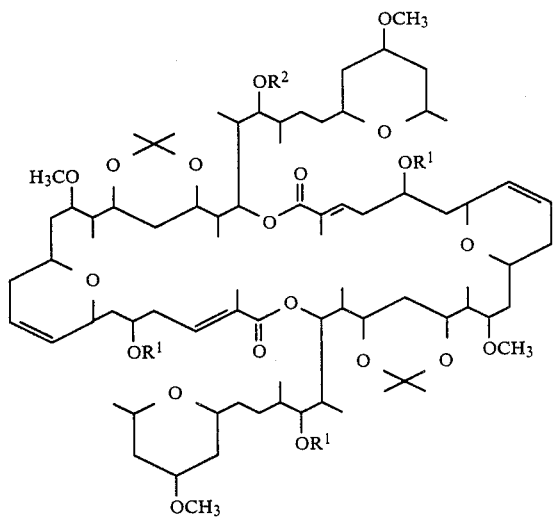

wherein:

$R^1 = R^2 = H$;

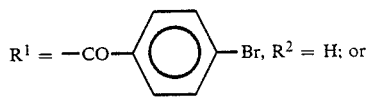

$R^1 = -CO-\phantom{}-Br, R^2 = H$; or

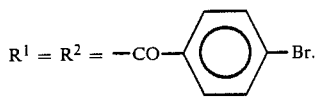

$R^1 = R^2 = -CO-\phantom{}-Br$.

3. A compound according to the formula:

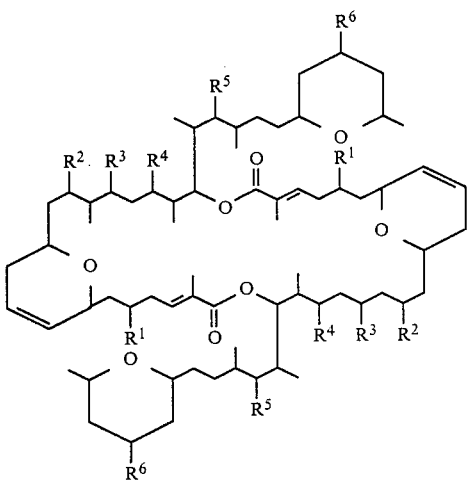

where $R^1$, $R^2$, $R^5$, and $R^6$ are the same or different selected from $-H$, $-OH$, $-OR$ and $-OCOR$, $R^3$ and $R^4$ are the same or different selected from $-H$, $-OH$, $-OR$ and $-OCOR$ or together may be $-O-C(CH_3)_2-O-$ and R is lower alkyl.

4. A compound of the formula:

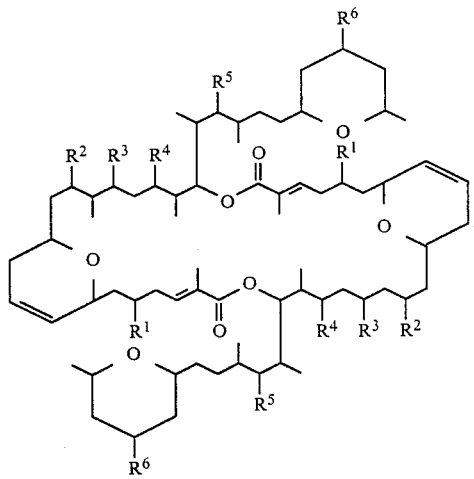

wherein $R^{1-6}$ are the same or different and are $-H$, $-OH$, $-OR$ or $-OCOR$ and R is lower alkyl, plus hydrogenation derivatives thereof wherein at least one double bond in the compound is reduced and derivatives thereof which have been oxidized, treated with an alkaline solution or treated with an acid solution.

5. An antitumor composition comprising, as an active ingredient, an effective antitumor amount of at least one compound of claim 4 and a non-toxic pharmaceutically acceptable carrier or diluent.

6. An antitumor composition comprising, as an active ingredient, an effective antitumor amount of at least one compound of claim 3 and anon-toxic pharmaceutically acceptable carrier or diluent 7. An antiviral composition comprising, as an active ingredient, an effective antiviral amount of at least one compound of claim 4 and a non-toxic pharmaceutically acceptable carrier or diluent.

8. An antiviral composition comprising, as an active ingredient, an effective antiviral amount of at least one compound of claim 3 and a non-toxic pharmaceutically acceptable carrier or diluent.

9. An antifungal composition comprising, as an active ingredient, an effective antifungal amount of at least one compound of claim 4 and a non-toxic pharmaceutically acceptable carrier or diluent.

10. An antifungal composition comprising, as an active ingredient, an effective antifungal amount of at least one compound of claim 3 and a non-toxic pharmaceutically acceptable carrier or diluent.

* * * * *